United States Patent
Pentoney, Jr. et al.

(10) Patent No.: US 7,518,727 B2
(45) Date of Patent: Apr. 14, 2009

(54) MULTICAPILLARY MULTILASER DETECTION SYSTEM

(75) Inventors: Stephen L. Pentoney, Jr., Chino Hills, CA (US); David L. Yang, Orange, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/680,013

(22) Filed: Feb. 28, 2007

(65) Prior Publication Data

US 2008/0203319 A1    Aug. 28, 2008

(51) Int. Cl.
*G01N 21/64* (2006.01)

(52) U.S. Cl. .................. 356/417; 356/318; 356/344; 250/458.1; 250/459.1; 250/461.2

(58) Field of Classification Search .................. 356/344, 356/416, 417, 418, 419
See application file for complete search history.

(56) References Cited

U.S. PATENT DOCUMENTS

| | | | |
|---|---|---|---|
| 5,091,652 A | 2/1992 | Mathies et al. | |
| 5,162,654 A | 11/1992 | Kostichka et al. | |
| 5,274,240 A | 12/1993 | Mathies et al. | |
| 5,582,705 A | 12/1996 | Yeung et al. | |
| 5,614,726 A | 3/1997 | Kaye et al. | |
| 5,675,155 A | 10/1997 | Pentoney, Jr. et al. | |
| 5,821,058 A | 10/1998 | Smith et al. | |
| 5,833,827 A | 11/1998 | Anazawa et al. | |
| 2003/0109773 A1* | 6/2003 | Samuels et al. | 600/315 |

FOREIGN PATENT DOCUMENTS

EP    0539743 A1    5/1993

WO    WO9403631    2/1994

OTHER PUBLICATIONS

MegaBACE 100 Instrument Administrator's Guide, Version 2.4, GE User Manual, 160 pages, Jun. 2002.
MegaBACE 1000 Instrument Maintenance and Troubleshooting Guide, Version 2.4, GE User Manual, 100 pages, Jun. 2002.
MegaBACE 4000 Instrument User's Guide, Version 3.2, GE User Manual, 350 pages, Dec. 2002.
Bashkin, J.S. et al., "Implementation of a capillary array electrophoresis instrument," J. Cap. Elec., 1996, pp. 61-68, vol. 3, No. 2.

(Continued)

*Primary Examiner*—F. L Evans
(74) *Attorney, Agent, or Firm*—Morrison & Foerster LLP

(57) ABSTRACT

A system for detecting electromagnetic radiation from samples comprising: a plurality of sample volumes, each of said sample volumes confined within a portion of a capillary column; a plurality of electromagnetic radiation sources; a mirror for receiving electromagnetic radiation from the electromagnetic radiation sources and for reflecting the electromagnetic radiation to the sample volumes; a scanner attached to the mirror; a parabolic reflector for collecting sample electromagnetic radiation from the sample volumes, the sample electromagnetic radiation being generated as a result of interaction of the reflected electromagnetic radiation with the sample volumes; a plurality of filters for filtering the sample electromagnetic radiation; and a plurality of detectors for detecting sample electromagnetic radiation from the sample volumes, each of the detectors being configured to receive sample electromagnetic radiation that has passed through a corresponding one of the plurality of filters and generate a signal upon receipt of sample electromagnetic radiation.

23 Claims, 6 Drawing Sheets

OTHER PUBLICATIONS

Crabtree, H.J. et al., "Construction and evaluation of a capillary array DNA sequencer based on a micromachined sheath-flow curvette," Electrophoresis, 2000, pp. 1329-1335, vol. 21.

Huang, X.C., et al., "Capillary Array Electrophoresis Using Laser-Excited Confocal Fluorescence Detection," Anal. Chem., 1992, pp. 967-972, vol. 64.

Huang, X.C., et al., "DNA Sequencing Using Capillary Array Electrophoresis," Anal. Chem., 1992, pp. 2149-2154, vol. 64.

Luckey, J.A. et al., "High speed DNA sequencing by capillary electrophoresis," Nucleic Acids Research, 1990, pp. 4417-4421, vol. 18, No. 15.

Marsh, M. et al., "High-throughput DNA sequencing on a capillary array electrophoresis system," J. Cap. Elec., 1997, pp. 83-89, vol. 4, No. 2.

Operator's Manual, NEN Model 4300 DNA Analyzer, Li-Core Manual, 136 pages, Jun. 1, 2002, Li-Core, Inc., Lincoln, Nebraska.

Prober, J.M. et al., "A System for Rapid DNA Sequencing with Fluorescent Chain-Terminating Dideoxynucleotides,"Science, 1987, pp. 336-341., vol. 238.

Swerdlow, H. et al., "Three DNA Sequencing Methods Using Capillary Gel Electrophoresis and Laser-Induced Fluorescence," Analytical Chemistry, 1991, pp. 2835-2841, vol. 63.

Zagursky, R.J. et al., "DNA Sequencing Separations in Capillary Gels on a Modified Commercial DNA Sequencing Instrument," BioTechniques, 1990, pp. 74-79, vol. 9.

Zhang, J. et al., "A multiple-capillary electrophoresis system for small-scale DNA sequencing and analysis," Nucleic Acids Research, 1999, pp. e36, i-vii, vol. 27, No. 24.

Zhang, J. et al., "Use of Non-Cross-Linked Polyacrylamide for Four-Color DNA Sequencing by Capillary Electrophoresis Separation of Fragments Up to 640 Bases in Length in Two Hours," Analytical Chemistry, 1995, pp. 4589-4593, vol. 67, No. 24.

International Search Report and Written Opinion for PCT/US08/55393, mailed Nov. 6, 2008, 7 pages.

* cited by examiner

MULTICAPILLARY MULTILASER DETECTION SYSTEM

BACKGROUND

The present invention is directed to a multicapillary fluorescent detection system, and more specifically, to a multicapillary multilaser detection system.

Capillary electrophoresis ("CE") has found widespread application in analytical and biomedical research and has been employed for the rapid separation and analysis of charged species including synthetic polynucleotides, DNA sequencing fragments, DNA restriction fragments, amino acids, optical isomers of dansyl amino acids, and the separation of proteins, viruses and bacteria. Micellar electrokinetic capillary chromatography, isoelectric focusing, and on-column derivatization can all be performed on CE columns.

The advantages of CE arise from the use of a small inside diameter (20-200 µm) capillary. Very high electric fields can be applied along small diameter fused-silica capillaries. Since the electrophoretic velocity of the charged species is proportional to the applied field, CE can achieve rapid, high-resolution separation. Considerable heat is generated by Joule heating. However, the large surface-to-volume ratio of the capillary channel and the use of thin capillary walls (50-150 µm), allows rapid heat dissipation when used in connection with cooling systems.

Automated DNA sequencing has gained widespread attention in recent years. Current methods for sequencing strands of DNA typically apply Sanger-Coulson type chemistries and electrophoretic methods to separate the DNA fragments generated during the sequencing reaction. Because capillary electrophoresis and particularly CE combined with laser induced fluorescence (CE-LIF) detection offers rapid charged species analyte separations and high detection sensitivity, it is particularly attractive as a separation technique in DNA sequencing applications. In order to take advantage of laser induced fluorescence some current DNA sequencing reactions involve fluorescently labeling DNA fragments and then separating and detecting the sequencing reaction products using CE-LIF techniques.

Even though CE separations are rapid, the throughput associated with CE based DNA sequencing is generally less than that of conventional slab gels when only one capillary forms the separation system. In order to overcome this limitation it has been suggested that multiple capillaries be used in parallel to achieve the desired throughput. Of course, the increased throughput of a multiple capillary CE system becomes a costly and cumbersome system when used in combination with a multiplicity of discrete source and detector elements. Moreover, the discrete source/detector element approach also becomes much more complicated when the requirement for multiple wavelength monitoring is added.

A multiple capillary CE-LIF system which utilizes a confocal fluorescence scanner is described in U.S. Pat. Nos. 5,091,652 and 5,274,240. These scanners rely on moving continuously each capillary in an array of capillaries across the light path of a laser. Alternatively, it has been suggested that the whole optical head be moved across the array of capillaries in a "sweep" scan (HPCE Meeting, San Diego, 1994). Both of these approaches require the movement of relatively heavy system components as one capillary is moved from the light source and the next capillary is moved into the light source. Necessarily, a large amount of time is consumed in moving the system components. It is likely that valuable separation information may be missed as a result of the lag time inherent in these systems. Moreover, the detection sensitivity attributed to fluorescence systems are somewhat compromised since the light source does not reside on an optimal part of the sample volume contained in each capillary, but is continuously scanned across the capillary.

Furthermore, since relatively heavy components are being moved in the prior art multicapillary detection systems, it is likely the momentum of the moving machinery will result in a gradual misalignment of the capillaries with respect to the light source or with the detector. Like the time delay problem, misalignments may lead to the loss of information and/or decreased sensitivity and increased detection limits. Also the motors and mechanisms required to move the capillaries necessarily result in additional cost associated with producing the scanner.

A multicapillary CE-LIF system utilizing a scanning mirror and parabolic reflector is described in U.S. Pat. No. 5,675,155, the entire contents of which are hereby incorporated herein by reference. This system relied on a spinning filter wheel in combination with a single detector for detection of multiple dyes. However, this system allows only a single dye to be detected at any time, and because of the need to switch filters only allows for a limited signal integration time. Additionally, because the filter elements are placed within the filter wheel, and the rotational velocity cannot be altered during the course of a run, the relative integration time for detection of the fluorophores is fixed for a given filter wheel. Changing filter wheels is an expensive and complex task.

Accordingly, it is desirable to provide an economical, flexible, highly sensitive, stable and rugged detection system for use in connection with high throughput separation systems. It is further desirable to provide an automated detection system for use in connection with multi capillary CE-LIF systems. Such a system should have the capability of providing multiple excitation wavelengths and detecting multiple emission wavelengths.

There is therefore a need for a detection apparatus that solves the shortcomings of the prior art.

SUMMARY

Accordingly, the present invention is directed to an improved system for detecting electromagnetic radiation from a plurality of analytical samples. The system, according to an embodiment of the present invention, has a plurality of sample volumes, each of said sample volumes confined within a portion of a capillary column; and a plurality of electromagnetic radiation sources. The system also has a mirror for receiving electromagnetic radiation from the electromagnetic radiation sources and for reflecting the electromagnetic radiation to the sample volumes. A scanner is attached to the mirror. A parabolic reflector collects sample electromagnetic radiation from the sample volumes, the sample electromagnetic radiation being generated as a result of interaction of the reflected electromagnetic radiation with the sample volumes.

A plurality of filters filter the sample electromagnetic radiation; and a plurality of detectors detect sample electromagnetic radiation from the sample volumes. Each of the detectors is configured to receive sample electromagnetic radiation that has passed through a corresponding one of the plurality of filters and generate a signal when receiving sample electromagnetic radiation.

Preferably, at least one of the plurality of filters allows a plurality of wavelength bands to pass. In an embodiment, the number of wavelength bands that are allowed to pass by one of the filters equals a maximum number of different labels detectable by the corresponding detector. Preferably, the number of detectors equals a maximum number of detectable labels excited by the one of the plurality of electromagnetic radiation sources that excites the greatest number of detectable labels.

Optionally, the electromagnetic radiation sources and the scanner are configurable so that at least one electromagnetic radiation source is directed to a sample volume for a longer time than at least one other electromagnetic radiation source. Additionally, the radiation sources and the scanner can be configured so that at least one of the electromagnetic radiation sources is directed to at least one of the sample volumes for a longer time than others of the sample volumes.

Preferably, the capillary columns form a capillary array with a plurality of coplanar side-by-side capillary columns. Optionally, the electromagnetic radiation sources are lasers. The scanner can be a galvo scanner. The system can also have a controller for assigning the signal from at least one of the plurality of detectors to a label based upon which electromagnetic radiation source was being reflected onto the sample volume when the detector generated the signal.

In additional embodiments, the system has a directing means for directing electromagnetic radiation from the electromagnetic radiation sources to the sample volumes. Optionally, the system is configured to detect electromagnetic radiation from an analytical sample in a capillary column, the system having a plurality of electromagnetic radiation sources oriented to direct electromagnetic radiation to the sample volume.

The present invention, according an embodiment, is also directed to an improved method of detecting the presence of samples contained in sample volumes. The method includes providing a detection system having: a plurality of the sample volumes, each of the sample volumes confined within a portion of a capillary column; a plurality of electromagnetic radiation sources; a mirror for receiving electromagnetic radiation from the electromagnetic radiation sources and for reflecting the electromagnetic radiation to the sample volumes; a scanner attached to the mirror; a parabolic reflector for collecting sample electromagnetic radiation from said sample volumes, said sample electromagnetic radiation generated as a result of interaction of the reflected electromagnetic radiation with the sample volumes; a plurality of filters for filtering the sample electromagnetic radiation; and a plurality of detectors for detecting sample electromagnetic radiation from the sample volumes, each of the plurality of detectors being configured to receive sample electromagnetic radiation that has passed through a corresponding one of the plurality of filters.

In the method, a first of the electromagnetic radiation sources sends first electromagnetic radiation to the mirror. The scanner aligns the mirror so that the first electromagnetic radiation is reflected from the mirror and focused on a first sample volume. Sample electromagnetic radiation is detected at the plurality of detectors, the sample electromagnetic radiation being generated as a result of interaction between the reflected first electromagnetic radiation and the sample.

Subsequently, a second of the electromagnetic radiation sources sends second electromagnetic radiation to the mirror. The scanner aligns the mirror so that the second electromagnetic radiation is reflected from the mirror and focused on a first sample volume. Sample electromagnetic radiation is detected at the plurality of detectors, the sample electromagnetic radiation being generated as a result of interaction between the reflected second electromagnetic radiation and the sample. Optionally, the first electromagnetic radiation and the second electromagnetic radiation are directed to the first sample volume for different durations.

Optionally, the method further includes causing the scanner to align the mirror so that the first electromagnetic radiation is focused on a second sample volume; detecting sample electromagnetic radiation at the plurality of detectors, the sample electromagnetic radiation generated as a result of interaction between the reflected first electromagnetic radiation and sample in the second sample volume; causing the scanner to align the mirror so that the second electromagnetic radiation is focused on a second sample volume; and detecting sample electromagnetic radiation at the plurality of detectors, the sample electromagnetic radiation generated as a result of interaction between the reflected second electromagnetic radiation and sample in the second sample volume. Optionally, at least one of the first electromagnetic radiation and the second electromagnetic radiation is focused on the first sample for a different duration than the second sample.

Thereafter, the scanner may repeatedly align the mirror sequentially so that the first and second electromagnetic radiation is reflected from the mirror and focused on the sample volumes and said sample electromagnetic radiation is detected from one sample at a time, in a sequential manner.

BRIEF DESCRIPTION OF THE DRAWINGS

A better understanding of the present invention will be had with reference to the accompanying drawings in which.

DETAILED DESCRIPTION

The present invention is directed to detection systems for use with high throughput electrophoretic separation devices containing multiple separation channels. Because laser induced fluorescence detection is typically the method of choice for achieving high sensitivity detection following capillary electrophoresis separation, the present discussion is limited to CE-LIF embodiments. Those skilled in the art will recognize that alternate multicapillary detection systems including ultraviolet (UV) and visible detection are equally applicable.

The detection system of the present invention involves moving a plurality of reflected excitation radiation beams sequentially and repetitively to a sample volume contained in each capillary in a multicapillary array. Emitted fluorescence is collected and delivered to a plurality of detectors that generate a signal whose magnitude is dependent on the amount of fluorescence. Because the plurality of excitation radiation beams are directed to each capillary without moving the capillary or moving the radiation sources, no bulky system components are moved. This feature provides improved system reliability and detection sensitivity.

Figure 1:
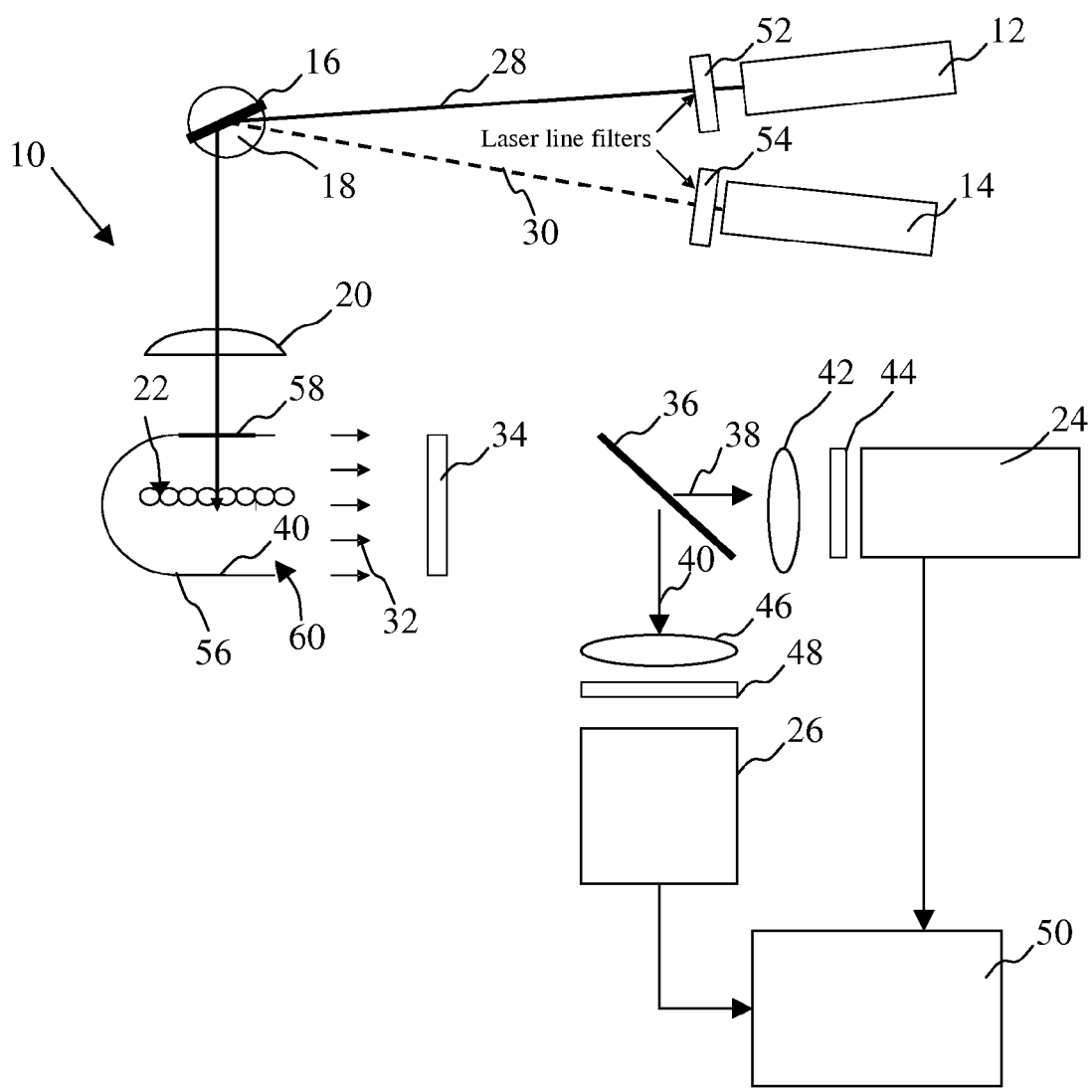
FIG. 1 is a schematic diagram of a multicapillary detection system according to an embodiment of the present invention.

FIG. 1 illustrates one embodiment of the present invention in which two lasers are used to excite a separated sample contained in a sample volume within each capillary of a capillary array. In this embodiment, two radiation sources are utilized to provide excitation radiation of two different wavelengths. Four fluorescent labels, two of which are capable of excitation at each of the wavelengths, are incorporated in the sample.

Referring to FIG. 1, a detection system 10 includes first and second laser radiation sources 12, 14, a mirror 16 mounted on a scanning means 18, a focusing lens 20, an array 22 of eight coplanar capillaries, and first and second detectors 24, 26. Laser sources 12, 14 direct excitation radiation beams 28, 30 respectively to a mirror 16 which is positioned by the scanning means 18 so that the excitation radiation beams 28, 30 are sequentially reflected from the mirror 16 to the focusing lens 20.

Figure 2:
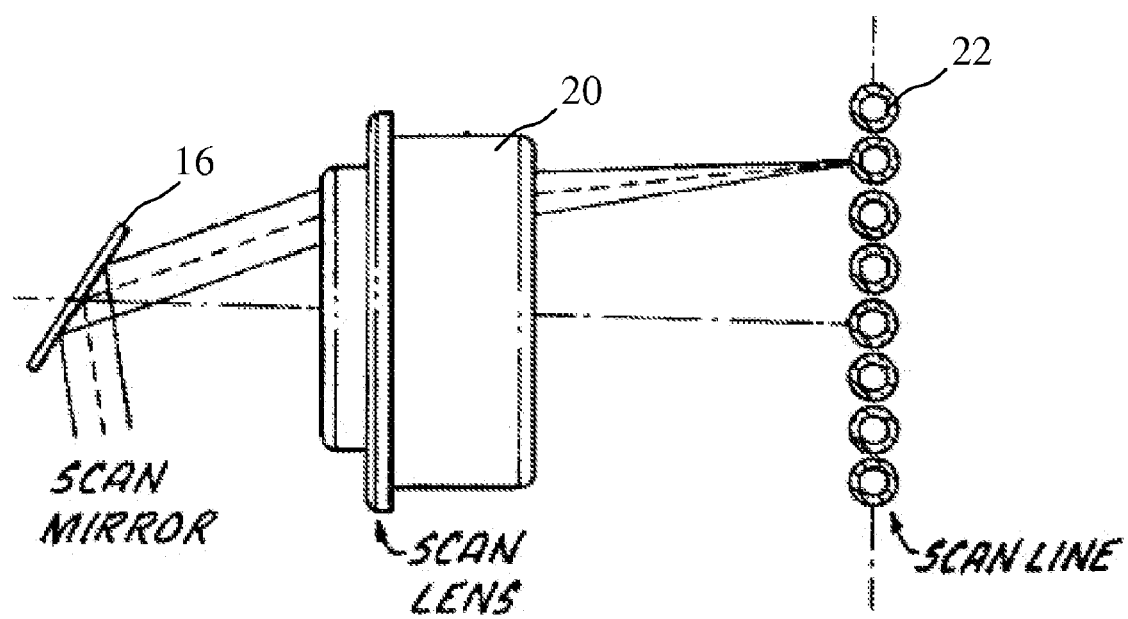
FIG. 2 illustrates the scan mirror, lens, and the orientation of the capillary array.

In FIG. 2, the focusing lens 20 is shown in greater detail bringing one of the reflected excitation beams 28, 30 in focus within a sample volume at the center of a selected capillary within the array 22. As shown in FIG. 1, the reflected excitation radiation beams 28, 30 interact with fluorescently labeled samples within the sample volume causing the sample to release emitted fluorescent radiation 32 which passes through a double block filter 34 and is directed to the first and second detectors 24, 26 by a beam splitter 36. The emitted radiation 32 is split by the beam splitter into first and second emitted beams 38, 40.

The first emitted beam 38 is directed through a first lens 42, through a first emission filter 44 to the first detector 24. The second emitted beam 40 is directed through a second lens 46, through a second emission filter 48 to the second detector 26. The first and second detectors 24, 26 provide signals in response to the presence of the emitted radiation 32. A computing system 50 receives the signals for processing.

The number of detectors needed is determined by the maximum number of detectable labels excited by one excitation radiation source. For example, if the excitation radiation source that excites the most labels excites fluorescence from three labels, then three detectors are needed.

Each emission filter corresponds to a particular detector. The number of wavelength bands passed by a particular filter is determined by the different labels to be detected by that detector. For example, if one detector detects three different labels excited by three different excitation radiation sources, with each label emitting excitation light in a different wavelength, then the filter corresponding to that detector is configured to allow passage of three different wavelength bands of excitation radiation.

Following release of the emitted radiation 32, the scanning means 18 causes the mirror 16 to direct the excitation radiation beams 28, 30 so that they are focused sequentially on the sample volume at the center of a different capillary in the capillary array. In such a manner scanning means 18 and attached mirror 16 are used to sequentially bring the excitation beams 28, 30 to a focus within the sample volumes of each capillary in the array.

From the foregoing description it can be seen that the detection system of the present invention incorporates an operating principle which involves focusing the first excitation radiation beam 28 to the first capillary center, then quickly repositioning the mirror so that the second excitation radiation beam 30 is aligned to focus to the first capillary center. The two excitation radiation beams are then stepped across the other capillaries in the array.

As used herein "step scanned" means that the excitation light sources dwell on a capillary in the array for a preset time period then are rapidly moved to the next capillary in the array where the excitation light sources again dwell for a preset period of time. The preset time period includes a measurement period or the time the excitation light is focused on a capillary in the array and during which time data is collected. The preset time can vary from capillary to capillary and from laser to laser. Data collection occurs during each preset time period for each capillary sample volume.

The speed of the galvo-scanner allows maximization of measurement periods while minimizing transition periods. Those skilled in the art will recognize that this approach allows all capillaries of a multi capillary array to be addressed using two or more laser sources and a predetermined number of detectors, the number of detectors being determined by the maximum number of labels excited by one laser. Because a step scan mode is utilized and sample volumes receive focused excitation radiation, maximum laser intensity is delivered to the capillary centers during each measurement period.

Detection system 10 preferentially includes filters 52, 54 located between the laser radiation sources 12, 14 and the mirror 16. The filters 52, 54 act to remove any radiation provided by the laser radiation sources 12, 14 having wavelengths outside of those necessary for excitation of fluorescently labeled sample.

To collect and collimate the emission radiation 32 and direct the emission radiation 32 to the detectors 24, 26, the present detector system preferably includes a high collection efficiency parabolic reflector 56. Each capillary of the array 22 is positioned about the focal point of the parabolic reflector 56. Reflected excitation radiation beams 28, 30 are directed through an entrance aperture 58 located in the parabolic reflector 56. Fluorescent emission radiation 32 from each capillary is collected by the parabolic reflector 56 and directed through an exit aperture 60 in the parabolic reflector 56.

Figure 3:
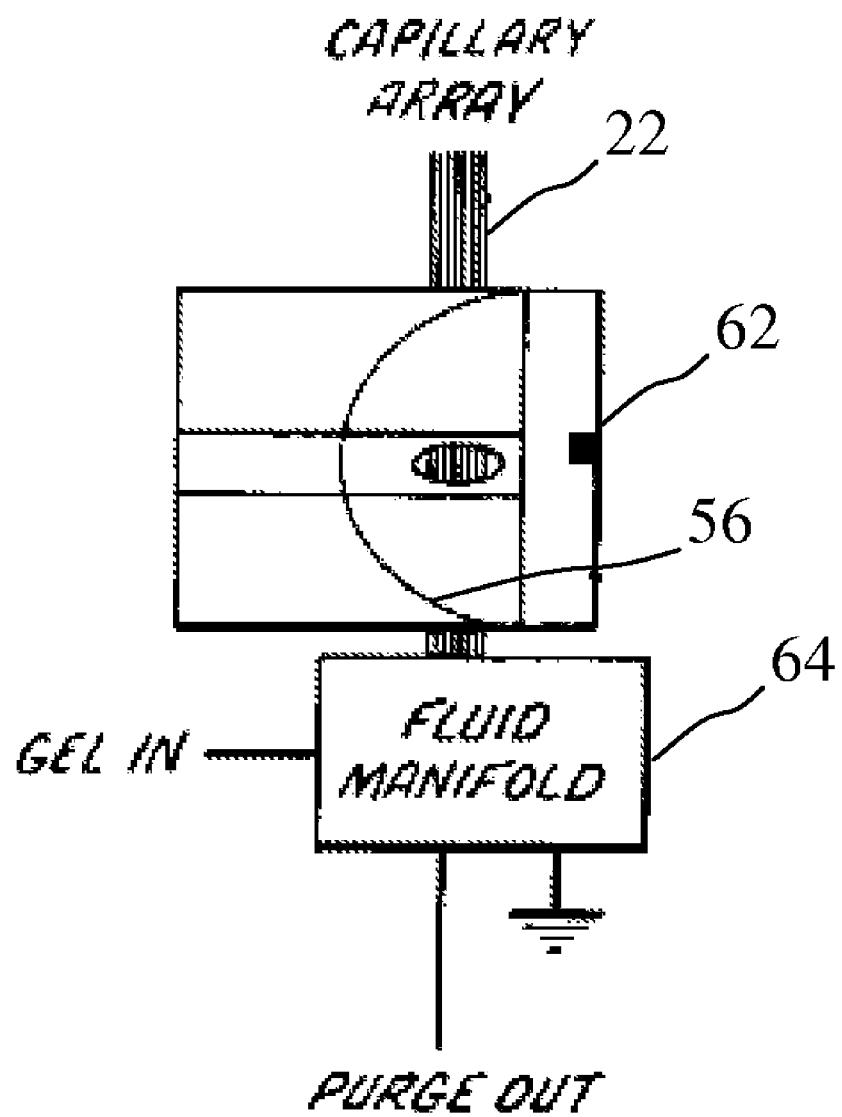
FIG. 3 is a schematic diagram of the parabolic mirror and array also showing the fluid manifold for controlling fluids into the capillaries.
Figure 4:
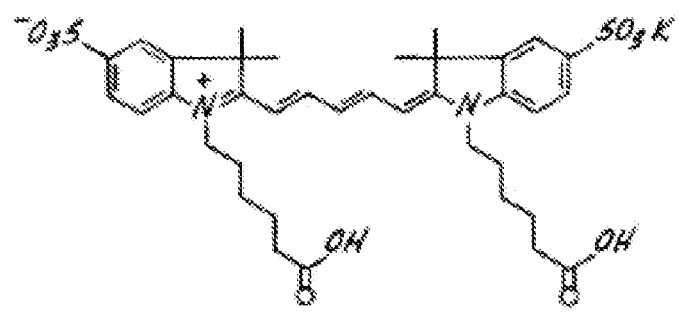
FIG. 4 illustrates the structure of fluorescent label $D_{673}$.
Figure 5:
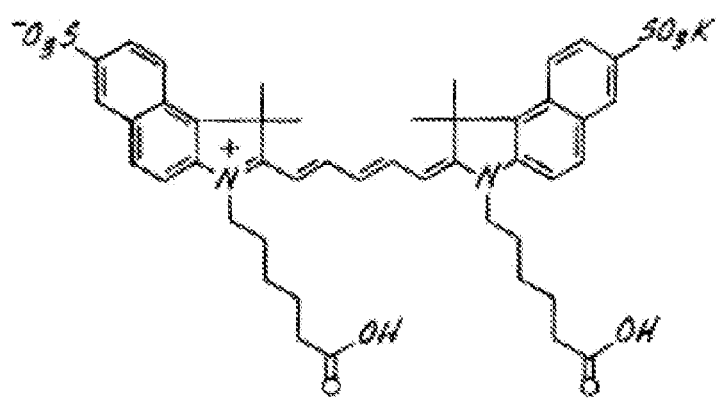
FIG. 5 illustrates the structure of fluorescent label $D_{715}$.
Figure 6:
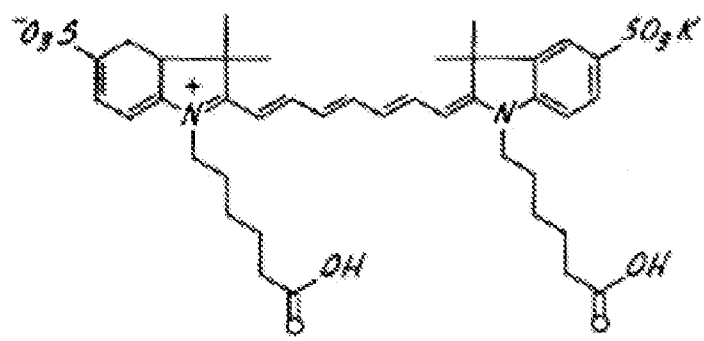
FIG. 6 illustrates the structure of fluorescent label $D_{775}$.
Figure 7:
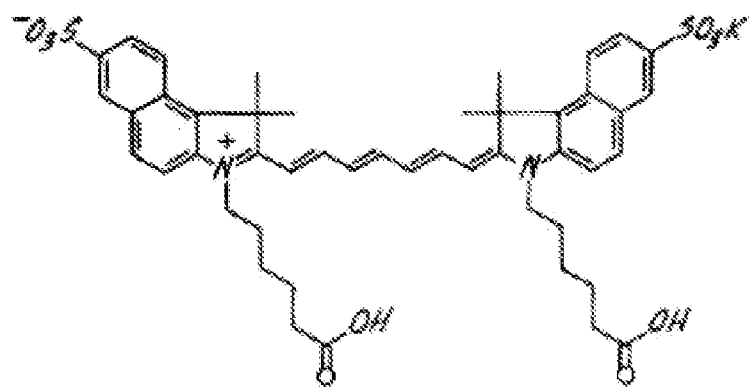
FIG. 7 illustrates the structure of fluorescent label $D_{820}$.

FIG. 3 shows the parabolic reflector of FIG. 1 with more detail. Capillary array 22 is shown positioned within the parabolic reflector 56. Additionally, as shown in FIG. 3, a black bar 62 (scatter bar) is placed in a plane orthogonal to the axis of the capillary array 22 to obstruct intense laser light scatter surrounding the capillaries in this plane. Also shown in FIG. 3 are components of the capillary electrophoresis fluid management system including a fluid manifold 64. Systems for supplying gel and current to the capillary array 22 are known to those skilled in the art.

In addition to the black bar 62, the system has other elements to limit laser scatter, background and unwanted radiation. As shown in FIG. 1, fluorescent emissions are directed through the double block filter 34 to the beam splitter 36 (preferably a 50/50 mirror) that splits the emission beam into two orthogonally directed beams. The beams are then directed through the first and second optical filters 44, 48 to the first and second detectors 24, 26. The double block and optical filters are selected to block any scatter or background excitation radiation from the laser source and to allow transmission of emission fluorescence from the excited samples in the capillaries.

In accordance with the present invention, the radiation sources 12, 14 can be any source of electromagnetic radiation having the desired emission wavelength or wavelength spectrum. Those skilled in the art will recognize that different fluorescent labels require different excitation energies or excitation wavelengths to obtain the desired emission properties. For purposes of the present invention, the radiation sources 12, 14 are preferentially laser diodes having a characteristic excitation wavelengths suitable for exciting fluorescence in the sample. Scanner 18 can be any device capable of very small precise movement such as a galvo scanner. Such scanners are particularly suitable in the practice of the present invention because they are a limited rotation servo motor capable of very rapid and precise movement. Mirror 16 is a plano mirror capable of receiving and reflecting the excitation radiation beams 28, 30.

Preferably, the excitation radiation sources are offset by from about 5 to about 10 degrees so that the scanner can switch from one excitation radiation source to the other. The amount of offset is variable depending on the capability of the scanner as long as the orientation of the light sources remains substantially constant throughout detection. Preferably, the excitation radiation source not being utilized for detection is switched off or directed to a beam dump (not shown).

For purposes of illustration and as shown in FIG. 1 the present embodiment utilizes a capillary array 22 of eight coplanar capillaries positioned side-by-side. The array is positioned so that the focused excitation beams 28, 30 are perpendicular to the length of the capillaries. The capillaries are fabricated of silica and have dimensions that can vary with the particular application. Suitable capillary dimensions can be typical of those utilized in capillary electrophoresis methods and include lengths of between 20 cm and 500 cm and diameters of between 20 µm and 500 µm. Preferred capillaries have relatively large wall thicknesses of 50 µm or greater.

The capillaries are connected to a single high voltage power supply which provides the potential for the electrophoretic field. In order for the excitation beam to enter the sample volume and for the emission beam to leave the sample volume, each column contains a transparent "window" surrounding the sample volume which is typical of silica capillaries used in CE applications.

Detectors suitable in the practice of the present invention can be any of a variety of devices used to generate signals from electromagnetic radiation including, but not limited to, charge coupled devices, avalanche photodiodes, photodiodes and photomultiplier tubes. Preferred detectors are photomultiplier tubes operated in a photon counting mode. Alternatively, a form of DC averaging detection can be utilized in the present detection systems. DC averaging detection involves an amplifier bandwidth which is fast enough to allow proper signal assignments with gating periods but which still possesses a sufficiently long time constant to allow extraction of accurate DC light levels from experimental photocurrents. This mode of detection does not offer the performance of photon counting but may offer a slight cost savings. DC averaging also provides superior performance at higher light levels for applications less demanding than DNA sequencing.

A multicapillary and multiwavelength detection system described herein provides a particularly suitable system for detecting DNA fragments obtained in DNA sequencing reactions where each of four nucleotide bases is identified by the emission wavelength of its unique fluorescent label. Four color DNA sequencing reactions and the subsequent separation of DNA fragments resulting from the reactions are known and will not be discussed in detail here.

The detector system of FIG. 1 is suitable for use in a four color DNA sequencing reaction. For purposes of illustration, the first excitation radiation source 12 is a laser capable of exciting a sample fluorescence attributed to first and second fluorescence dyes. Similarly, the second excitation radiation source 14 is a laser capable of exciting a sample fluorescence attributed to third and fourth fluorescent dyes.

During operation, the first excitation radiation source 12 is turned on and directed onto the mirror 16. Reflected excitation beam 28 passes through the entrance aperture 58 of the parabolic reflector 56 and onto a sample volume of a first capillary within capillary array 22, as described above. Fluorescence emission radiation 32 from the sample volume of the first capillary is collected and passed through the double block filter 34 to the beam splitter 36, and then through the first and second emission filters 44, 48 to the first and second detectors 24, 26.

The first and second emission filters 44, 48 block light at the wavelength of the first excitation radiation source 12 and transmit fluorescence emitted by the first and second fluorescent dyes respectively. Fluorescence transmitted by the first and second emission filters 44, 48 is detected at the detectors 24, 26 and signals from the detectors are transmitted to the computing system 50 for processing.

After the detectors 24, 26 detect fluorescence emissions attributed to the first and second fluorescence dyes, respectively, in the first capillary in the array, the first excitation radiation source 12 is turned off and the second excitation radiation source 14 is turned on. The beam from the second excitation source 14 is directed onto the first capillary, as described above. Fluorescence from the excited capillary is collected and passed through the double block filter 34 to the beam splitter 36, and then through the first and second emission filters 44, 48 to the detectors 24, 26.

The first and second emission filters 44, 48 block light at the wavelength of the second excitation radiation source 14 and transmit fluorescence emitted by the third and fourth fluorescent dyes respectively. Fluorescence transmitted by the first and second emission filters 44, 48 is detected at the detectors 24, 26 and signals from the detectors are transmitted to the computing system.

After measurements corresponding to each of the four dyes have been taken, the second excitation radiation source 14 is turned off, the scanning means 18 moves the mirror 16 so that the mirror directs the reflected excitation radiation beam 28 onto a second capillary in the array and the first excitation radiation source 12 is turned on. The sequence described above is then repeated until measurement for each of the four dyes are taken in the second capillary. This sequence is repeated for each of the capillaries in the array. After measurement for each of the four dyes in each of the capillaries in the array are taken the scanning means 18 moves the mirror 16 so that it is positioned to direct the reflected beam onto the first capillary in the array. The whole sequence is then repeated until data collection is completed.

Those skilled in the art will recognize that the foregoing description advantageously provides detection data for each of multiple fluorescence dyes in each of multiple capillaries contained in an array of capillaries. Each fluorescent signal is assigned to its respective capillary by synchronizing the galvo-scanner positioning with the photon counter gating periods. In this manner the location and identity of the fluorescent sample in each sample volume can be identified at any time period during the analytical procedure. The combination of galvo scanner, mirror and the focusing lens allows rapid sample volume excitation and detection. The length of time required to make a capillary to capillary transition is about 400 µsec.

Several alternative approaches for light delivery and fluorescence collection may be used in the present invention. For example, alternative directing means for directing excitation radiation beams to the sample volumes include: the use of a fiber optic switching device; the use of a binary optic beamsplitter; and the use of a spinning, faceted mirror.

As noted above, fluorescent dyes capable of being attached as labels to sample components so that they can be easily detected subsequent to their electrophoretic separation are advantageously used in the present invention. The choice of fluorescent dyes for any given application depends upon the sample components of interest, the detection system configuration, and the availability of specific lasers and detectors. Typically, fluorescent labels are selected for their excitation requirements and their emission characteristics. Moreover, one skilled in the art will realize that different lasers and filters or different combinations of lasers and filters may be required to accommodate the different properties of the fluorescent labels or combination of labels.

Preferably, fluorescent labels utilized in a multiple fluorescent dye system of the present invention are capable of utilizing common excitation radiation wavelengths and provide emission radiation of wavelengths sufficiently different to allow their resolution. Fluorescent labels and labeling chemistry are well known in the art and will not be discussed further here. A wide variety of fluorescent dyes and fluorescent labels are commercially available and in many cases they can be purchased in an activated form. This provides a ready means for their attachment to samples prior to their electrophoretic separation.

Advantageously, the detection system of the present invention can be used to align the capillaries so that each capillary is in an optimum position with respect to the laser excitation beam and detector. U.S. Pat. No. 5,614,726, which is hereby incorporated herein by reference, describes such an alignment procedure. Once the capillaries used in the present invention are aligned in accordance with the method taught in the referenced patent application, they remain aligned for a substantial period of time. This is because the present invention does not rely upon bulky component movement in order to scan the capillaries. Such bulk movement causes frequent misalignment of component parts which results in loss of sensitivity and can lead to total loss of signal.

As already mentioned, a preferred application of the present invention is the analysis of fluorescently labeled DNA fragments resulting from Sanger Coulson DNA sequencing reaction chemistries. Those skilled in the art will appreciate that extremely low detection limits are required to successfully apply CE based separations to DNA sequencing applications. The present invention provides these low detection limits and advantageously results in high sample throughput.

It is generally accepted that, when using CE/LIF based DNA sequencing, an optical system capable of exhibiting fluorescent label concentration detection limits in the 10 pM (picomolar) range will produce electropherograms with sufficient signal-to-noise ratios to allow sequence calling from standard scale sequencing reactions.

Figure 8:
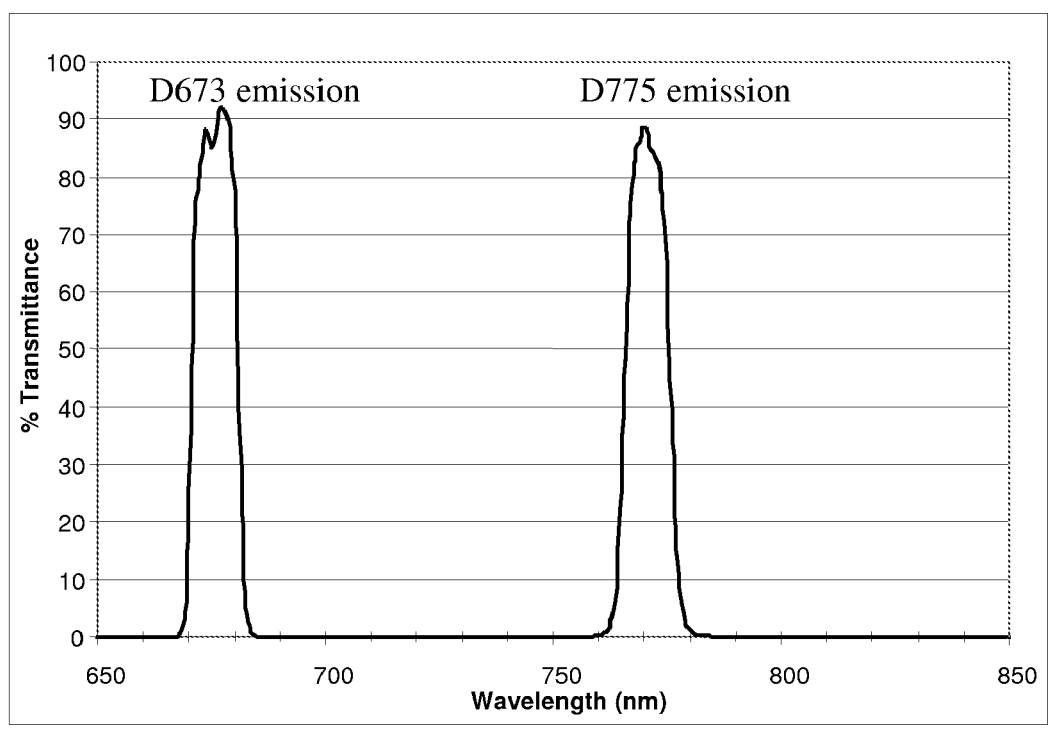
FIG. 8 is a plot of transmittance versus wavelength of a fluorescent filter usable with the system of FIG. 1 for detecting $D_{673}$ and $D_{775}$ emissions.
Figure 9:
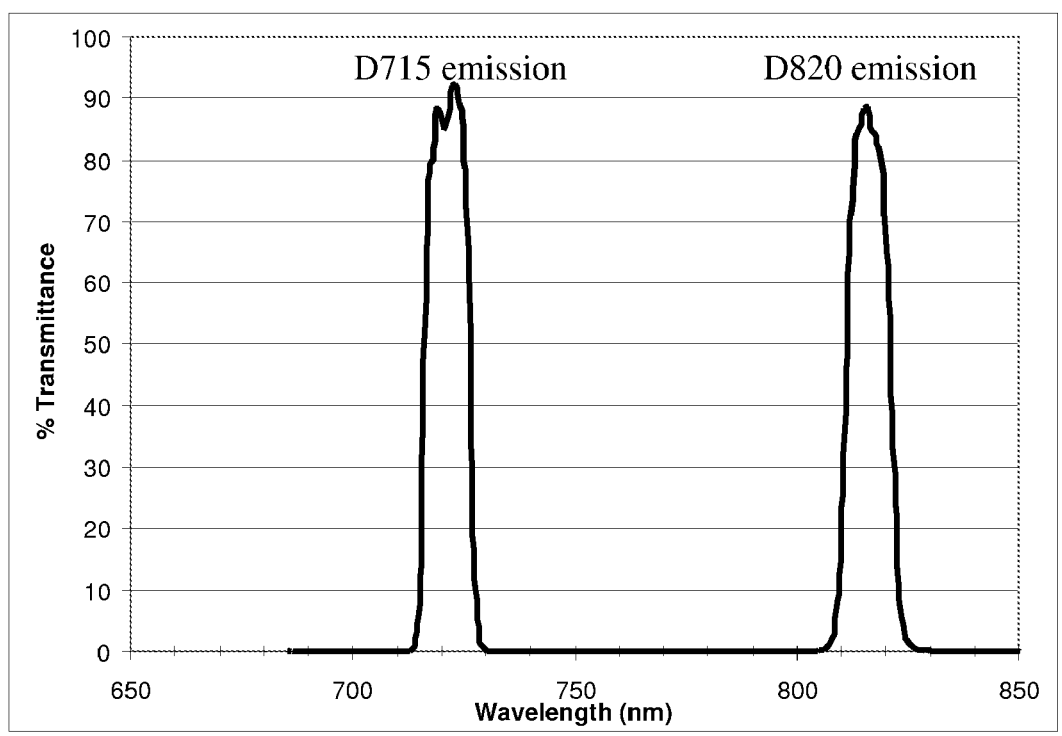
FIG. 9 is a plot of transmittance versus wavelength of a fluorescent filter usable with the system of FIG. 1 for detecting $D_{715}$ and $D_{820}$ emissions.

A system according to an embodiment of the present invention can utilize a 650 nm laser and a 750 nm laser. Four fluorophores that can be used are $D_{673}$, $D_{715}$, $D_{775}$ and $D_{820}$. The subscripts here refer generally to the wavelength of the emission maximum. For example, the fluorescence maximum for the fluorophore $D_{673}$ is 673 nm. Structures of the four fluorophores are shown in FIGS. 4, 5, 6, and 7, respectively. The first two fluorophores, $D_{673}$ and $D_{715}$, are well excited with the 650 nm laser. The last two fluorophores, $D_{775}$ and $D_{820}$, are well excited with the 750 nm laser. A transmittance spectrum of a filter usable for the first emission filter 44 is shown in FIG. 8. A transmittance spectrum of a filter usable for the second emission filter 48 is shown in FIG. 9.

During the course of the separation and detection of compounds labeled with the four fluorophores, when the 650 nm laser is striking the sample volume, fluorescence detected by the first detector 24 is assigned to fluorophore $D_{673}$ and fluorescence detected by the second detector 26 is assigned to fluorophore $D_{715}$. When the 750 nm laser is striking the sample volume, fluorescence detected by the first detector 24 is assigned to fluorophore $D_{775}$ and fluorescence detected by the second detector 26 is assigned to fluorophore $D_{820}$. Optionally, the dynamic assignment of detected fluorescence to particular fluorophores is done by the computing system 50 based on the laser striking the sample.

The present invention is not to be limited to the specific embodiments which are shown or described above and which are merely illustrative. Various and numerous other arrangements may be devised by one skilled in the art without departing from the spirit and scope of this invention. For example, the detection system of the present invention may be applicable to detection based upon phosphorescent labels, chemiluminescent labels, visible labels, or electrochemiluminescent labels.

The detection system of the present invention has utility in numerous applications in addition to the separation and detection of DNA fragments resulting from DNA sequencing reactions. In the discussion which follows, a number of applications are described, all of which are benefited by the high throughput and detection sensitivity characteristic of the present invention.

One application for a CE-LIF system equipped with a detection system as described herein involves the analysis of DNA amplification products (for example, PCR products).

Another application is DNA size analysis. Utilizing the detection system of the present invention for such an application allows the sample and standard to be run together in parallel, using different fluorescent labels to distinguish them.

There are several advantages of the present system and method over prior art. For example, no spinning filter wheel is required. Additionally, count times may be increased and varied. For example, count time can be increased for a particular laser or for a particular sample volume as explained below.

Currently on Beckman Coulter's CEQ Genetic Analysis system, a spinning filter wheel with four emission bandpass filter elements spinning at 2 Hz, is placed in front of a single detector and used to identify the fluorescence from four labeled compounds. Since the data acquisition rate is 2 Hz, 0.5 seconds is the total amount of time to collect data from each of the four emission wavelengths for all eight capillaries. Thus, at best, only (0.5 sec)/[(8 capillaries)(4 wavelengths/capillary)] or 0.0156 seconds of integration time is available for integration of fluorescence for any emission wavelength for any capillary. This is evenly distributed among all capillaries and all emission wavelengths.

The actual integration time is less than 0.0156 seconds since time is required for the filter wheel to rotate so that only one filter element is in front of the detector. In practice, an integration time of approximately 0.010 seconds is used.

However, in some applications, the amount of some fluorophores may be smaller than others. Thus, it may be desirable to increase the integration time for some detection wavelengths relative to others.

To change the integration period for a set of fluorophores, $D_{775}$ and $D_{820}$, for example, on the CEQ system would require a new filter wheel in which the filter elements for those two collection wavelengths is increased while the size of the filter elements for the other two emission wavelengths are decreased, thus increasing the residence time of those filters in front of the detector of the filters for $D_{775}$ and $D_{820}$. Unfortunately, changing filter wheels is a complex and expensive task and therefore an undesirable solution. However, by using the system and methods described herein, an increase in integration time for detection of fluorophores $D_{775}$ and $D_{820}$, for example, may be accomplished by simply increasing the time the 750 nm laser illuminates the sample volume.

As previously described, a parabolic reflector collects and directs fluorescence emissions to a detector. Because the parabolic reflector has a finite focal point, sample volumes away from the focal point have a lower fluorescence collection efficiency than sample volumes near the focal point. It has been determined that if the same concentration of sample is in all eight capillaries, the outer capillaries collect approximately one-third the amount of light compared to the center capillary.

Currently, there are no good ways to eliminate this bias. One undesirable method would be to translate the parabolic reflector during the course of data acquisition, but the accurate movement of this relatively large mass would be difficult. However, using the system and method described herein, this problem is remedied by increasing the dwell time of the lasers on the sample volumes further away from the parabolic reflector's focal point relative to those sample volumes close to the focal point.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except combination where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. A system for detecting electromagnetic radiation from a plurality of analytical samples, the system comprising:
   a) a plurality of sample volumes, each of said sample volumes confined within a portion of a capillary column;
   b) a plurality of electromagnetic radiation sources;
   c) a scanner configured to receive electromagnetic radiation from the electromagnetic radiation sources and to direct the electromagnetic radiation to the sample volumes;
   d) a parabolic reflector for collecting sample electromagnetic radiation from said sample volumes, said sample electromagnetic radiation generated as a result of interaction of the directed electromagnetic radiation with the sample volumes;
   e) a plurality of filters for filtering the sample electromagnetic radiation, at least one of the plurality of filters allowing a plurality of wavelength bands to pass; and
   f) a plurality of detectors for detecting sample electromagnetic radiation from the sample volumes, each of the plurality of detectors being configured to:
      (i) receive sample electromagnetic radiation that has passed through a corresponding one of the plurality of filters; and
      (ii) generate a signal upon receipt of sample electromagnetic radiation.

2. A system of claim 1, wherein the electromagnetic radiation sources and the scanner are configured so that at least one electromagnetic radiation source is directed to a sample volume for a longer time than at least one other electromagnetic radiation source.

3. A system of claim 1, wherein the radiation sources and the scanner are configured so that at least one of the electromagnetic radiation sources is directed to at least one of the sample volumes for a longer time than others of the sample volumes.

4. A system of claim 1, wherein the number of wavelength bands that are allowed to pass equals the number of electromagnetic radiation sources.

5. A system of claim 1, wherein the number of detectors equals a maximum number of detectable labels excited by the one of the plurality of electromagnetic radiation sources that excites the most detectable labels.

6. A system of claim 1, wherein:
   the capillary columns form a capillary array comprising a plurality of coplanar side-by-side capillary columns; and
   the electromagnetic radiation sources are lasers.

7. A system of claim 1, wherein the scanner is a galvo scanner.

8. A system of claim 1, wherein the parabolic reflector further comprises an entrance aperture for the reflected electromagnetic radiation to contact each of said sample volumes.

9. A system of claim 1, wherein the detectors are selected from the group consisting of photomultiplier tubes, charged coupled devices, and photodiodes.

10. A system of claim 1, further comprising a controller for assigning the signal from at least one of the plurality of detectors to a label based upon which electromagnetic radiation source was being directed onto the sample volume when the detector generated the signal.

11. A system for determining a light excitable label in a biological sample, the system comprising:
   a first light source arranged to illuminate the biological sample and cause a first light excitable label to emit light;
   a second light source arranged to illuminate the biological sample and cause a second light excitable label to emit light;
   a beam splitter arranged to receive the emitted light, wherein said beam splitter divides said emitted light into at least a first beam and a second beam;
   a filter arranged to receive said first beam, wherein said filter is configured to pass at least a first wavelength band and a second wavelength band, wherein said first wavelength band of said filter is designed to pass emitted light excited by the first light source and said second wavelength band of said filter is designed to pass emitted light excited by the second light source; wherein said first wavelength band and said second wavelength band are separate bands; and
   a photo-detector arranged to receive the filtered first beam.

12. A system of claim 11, wherein the first light source illuminates the biological sample for a longer time than the second light source illuminates the biological sample.

13. A system of claim 11, wherein the biological sample is contained in a capillary.

14. A system of claim 11, wherein the beam splitter is wavelength neutral.

15. A system of claim 11, further comprising a reflector arranged to direct the emitted light toward the beam splitter.

16. A system of claim 15, wherein the reflector is a parabolic reflector.

17. A system of claim 11, wherein the first light source is arranged to illuminate a second biological sample and the first light source illuminates the biological sample for a longer time than the first light source illuminates the second biological sample.

18. A system of claim 11, further comprising a scanner arranged to direct light from the first and second light sources to the biological sample.

19. A method of determining a light excitable label in a biological sample, the method comprising:
- illuminating the biological sample sequentially with a first light followed by a second light, wherein the first light excites a first light excitable label to emit light in a first wavelength band and the second light excites a second light excitable label to emit light in a second wavelength band;
- splitting the emitted light into at least a first beam and a second beam;
- filtering the first beam through a filter configured to pass at least the first wavelength band and the second wavelength band, wherein the first wavelength band and the second wavelength band are separate bands; and
- detecting the filtered first beam.

20. A method of claim 19, wherein the first light illuminates the biological sample for a longer time than the second light illuminates the biological sample.

21. A method of claim 19, wherein the step of illuminating the biological sample comprises illuminating a second biological sample and the biological sample is illuminated for a longer time than the second biological sample is illuminated.

22. A system of claim 11, further comprising:
- a second filter arranged to receive said second beam, wherein said second filter is configured to pass at least a third wavelength band and a fourth wavelength band, wherein said third wavelength band of said filter is designed to pass emitted light excited by the first light source and said fourth wavelength band of said filter is designed to pass emitted light excited by the second light source; and
- a second photo-detector arranged to receive the filtered second beam.

23. A method of claim 19, wherein the first light additionally excites a third excitable label to emit light in a third wavelength band and the second light additionally excites a fourth light excitable label to emit light in a fourth wavelength band;
- filtering the second beam though a filter configured to pass at least the third wavelength band and the fourth wavelength band, wherein the third wavelength band and the fourth wavelength band are separate bands; and
- detecting the filtered second beam.

* * * * *